United States Patent [19]

Gall

[11] 4,001,262
[45] Jan. 4, 1977

[54] PROCESS FOR THE PRODUCTION OF 1-[(DIMETHYLAMINO)METHYL]-6-PHENYL-4H-TRIAZOLO[4,3-a][1,4]-BENZODIAZEPINE

[75] Inventor: Martin Gall, Kalamazoo, Mich.

[73] Assignee: The Upjohn Company, Kalamazoo, Mich.

[22] Filed: Oct. 20, 1975

[21] Appl. No.: 623,972

[52] U.S. Cl. .................. 260/296 T; 260/308 R; 424/263; 424/269
[51] Int. Cl.² ............ C07D 213/72; C07D 403/06
[58] Field of Search .............. 260/296 T, 308 R

[56] References Cited
OTHER PUBLICATIONS

B387,761, Jan. 1975, Gall, 260/308 R.
B471,494, Mar. 1976, Hester, 260/308 R.
Schreiber et al., Angew. Chem. Internat. Edit. vol. 10, pp. 330–331 (1971).
Masui et al., Chemical Abstracts vol. 72, Abst. No. 78250n (1970).
Allgeier et al., Chemical Abstracts vol. 77, Col. 126711r (1972).
Allgeier et al., Chem. Abstracts vol. 82, Abst. No. 156399r (1975).

*Primary Examiner*—John D. Randolph
*Attorney, Agent, or Firm*—Hans L. Berneis

[57] ABSTRACT

A process for the preparation of 1-[(dimethylamino)-methyl]-6-substituted-4H-s-triazolo[4,3-a][1,4]benzodiazepine which comprises the reaction of a 4H-s-triazolo[4,3-a][1,4]benzodiazepine with the reagent

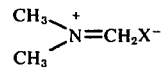

wherein X⁻ signifies the anion of a monovalent acid.

7 Claims, No Drawings

PROCESS FOR THE PRODUCTION OF 1-[(DIMETHYLAMINO)METHYL]-6-PHENYL-4H-TRIAZOLO[4,3-A][1,4]-BENZODIAZEPINE

BACKGROUND OF THE INVENTION

FIELD OF THE INVENTION

This invention is directed to a novel chemical process and is particularly concerned with the production of the anti-depressive anxiolytic 1-[(dimethylamino)methyl]-6-phenyl-4H-s-triazolo[4,3-a][1,4]benzodiazepines.

The process of this invention can be illustratively represented as follows:

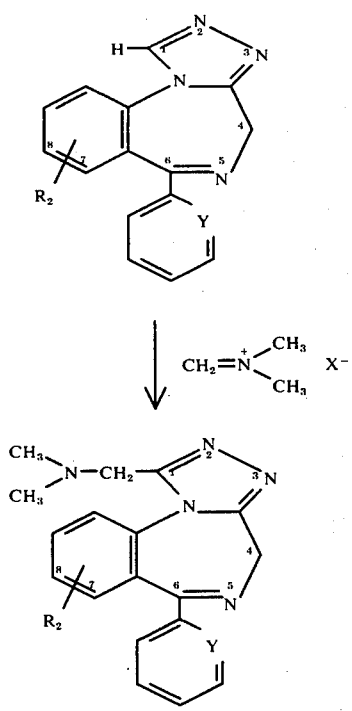

wherein $X^-$ is the anion of a monovalent organic or inorganic acid, preferably the anions of hydrochloric, hydrobromic, and hydriodic and trifluoroacetic acid; wherein Y is nitrogen or

in which $R_1$ is hydrogen, chloro, or fluoro; wherein $R_2$ is hydrogen, fluoro, chloro, bromo, trifluoromethyl, or nitro.

The novelty of this invention consists in using specific conditions with a specific reagent while applying a Mannich Type reaction to prepare as the major product compound of formula 11. The use of the Mannich reaction in this case is not new. Application Ser. No. 387,761, filed Aug. 13, 1973, now Ser. No. B 387,761, published Jan. 28, 1975, discloses the use of the Mannich reaction for the addition of an aminoalkyl group to a triazole ring. When the conditions of this invention (Ser. No. B 387,761 ) are applied to the compounds of formula I of this invention the desired products of formula II are not obtained, but instead compounds of the formula III.

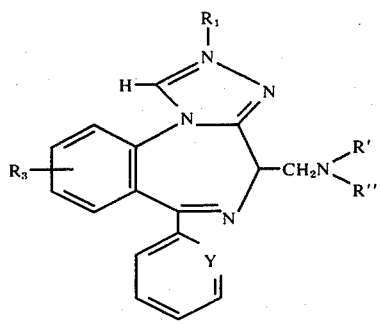

Only with the present reagent IV and the conditions further on described the compounds of formula II are obtained. The reagent used has the formula IV;

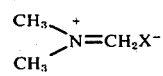

wherein $X^-$ is any suitable anion of a monovalent inorganic or organic acid such as hydrochloric, hydrobromic, hydriodic, trifluoroacetic, acetic, tetrafluoroboric, benzoic, $HPF_6$, perchloric, chloric, $HSbCl_6$ and the like. Such reagents are disclosed in the art, e.g. Böhme, H, et al., Chem. Ber. 105, 2233, (1972). Böhme, H. et al., Chem. Ber. 93, 1305 (1960); Böhme, H., Tetrahedron Lett. 2785 (1972); Volz, H. and Kiltz, H., Tetrahedron Lett. 1917 (1970) and Am. Chem. 752, 86 (1971); Huisgen, R., Kolbeck, W. Tetrahedron Lett. 783 (1965); Ahond, A., et al., J. Amer. Chem. Soc., 90, 5622 (1968); Jaser, Y., Chem. Comm. 253 (1974); Eschenmoser, A., et al., Angew. Chem. Int. Ed. (Eng) 10, 330, (1971).

In order to obtain a high yield in the reaction I → II, , specific reaction conditions must be applied. Under other conditions the above described reagents can add at the 4-position only, or simultaneously in the 1- and 4-positions of compound I thus providing products of lesser interest than those defined by formula II.

PREFERRED EMBODIMENT OF THE INVENTION

The preferred compounds of formula II have the substituent $R_2$ in the 8-position. These compounds of formula II possess sedative, tranquilizing and also antidepressant activity as disclosed in great detail in U.S. Pat. No. 3,842,090.

They are particularly useful in the treatment of mammals, including man, to alleviate anxieties and/or depressions in oral or injectable dosages of 0.02–1 mg./kg., or preferredly 0.05 to 1 mg./kg.

In carrying out the process of the present invention a compound of the formula I is treated with a compound of the formula IV under special and very limited conditions explained herein below:

1. The solvent can be dimethylformamide, dimethyl acetamide, N-methylpyrrolidone. The preferred solvent is dimethylformamide. (Ethereal solvents did not provide any compound).

2. The yield depends on the temperature and time. The highest result of the desired product was obtained by stirring the reaction mixture for 3 days at 50° to 60° C.

In general, the experimental conditions besides the specific solvent dimethyl formamide requires that the reaction be carried out between 50° to 100° C. during ½ to 100 hours.

Furthermore, it was discovered that the higher yields are obtained when the time of reaction is increased, providing the temperature of the reaction is decreased.

The reagent of formula IV is

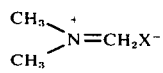

in which $X^-$ is an anion of monovalent organic or inorganic acid. Such acids are e.g. hydrochloric, hydrobromic, hydriodic, perchloric, periodic, toluenesulfonic, benzoic, tetrafluoroboric, hexachloroantimonic ($S6Cl_6$), hexafluorophosphoric ($HPF_6$), trifluoroacetic or acetic or the like. Preferred are the anions of trifluoroacetic acid or of hydrogen halides, i.e. hydrochloric, hydrobromic, hydriodic acid.

The starting compounds of this invention are prepared as e.g. shown in British Pat. Nos. 1,291,631; 1,298,366; specifically 1,298,366 and U.S. Pat. No. 3,734,922.

The following examples illustrate this invention, but should not be construed as limiting.

EXAMPLE 1

1-(Dimethylamino)methyl-8-chloro-6-phenyl-4H-s-triazolo[4,3-a][1,4]benzodiazepine 1. Preparation of the reagent dimethylmethylene ammonium chloride A solution of 4.08 g. (40.0 mmol) of bis(dimethylamino)methane in 50 ml. of dimethylformamide was treated, at 0° C., with 2.824 ml. (40.0 mmol) of acetyl chloride to give a solution of dimethylmethylene ammonium chloride.

2. To this solution was added 5.86 g. (20 mmol) of 8-chloro-6-phenyl-4H-s-triazolo[4,3-a][1,4]benzodiazepine The mixture was heated in an oil bath between 55°–60° C. for 72 hours, quenched on ice, neutralized with a 10% aqueous sodium hydroxide solution and chromatographed over 500 g. of silica gel by eluting with 1 liter of 3% methanol/chloroform mixtures to give 1-(dimethylamino)methyl-8-chloro-6-phenyl-4H-s-triazolo[4,3-a][1,4]benzodiazepine of melting point 171°–172.5°, yield 68.7%.

Anal. calcd. for $C_{23}H_{26}ClN_5$: C, 64.86; H, 5.16; Cl, 10.08; N, 19.90. C, 64.86; H, 5.16; Cl, N, Found: C, 64.91; H, 5.35; Cl, 10.03; N, 19.53

EXAMPLE 2

1-[(Dimethylamino)methyl]-8-chloro-6-(o-chlorophenyl)-4H-s-triazolo[4,3-a][1,4]benzodiazepine In the manner given in Example 1, 8-chloro-6-(o-chlorophenyl)-4H-s-triazolo[4,3-a][1,4]benzodiazepine was added to a solution of dimethylmethylene ammonium chloride and heated for 100 hours from 55°–60° C. The mixture was quenched on ice, neutralized with a 10% aqueous sodium hydroxide solution and chromatographed over 50.0 g. of silica gel by eluting with 1 l. of 3% methanol/97% chloroform mixture to afford 8-chloro-1-[(dimethylamino)methyl]-6-(o-chlorophenyl)-s-triazolo[4,3-a][1,4]benzodiazepine which was crystallized as a dihydrobromide salt of melting point 199°–201° C.

EXAMPLE 3

1-(Dimethylamino)methyl-8-bromo-6-(2-pyridyl)-4H-s-triazolo[4,3-a][1,4]benzodiazepine A solution of 0.51 g. (5.0 mmol) of $[(CH_3)_2N]_2CH_2$ in 10 ml. of dimethylformamide was cooled to 0° C. and stirred for 10 minutes. To this solution, 0.355 ml. (0.39 g., 5.0 mmol) of acetyl chloride was added dropwise over a period of 15 minutes under a nitrogen atmosphere to give dimethylmethylene ammonium chloride.

To a suspension of this reagent in 10 ml. of dimethylformamide was added 3.00 mmol of 8-bromo-6-(2-pyridyl)-4H-s-triazolo[4,3-a][1,4]benzodiazepine. The mixture was heated to 80° for a total of 24 hours, then quenched in cold water, neutralized with a 10% aqueous sodium hydroxide solution and extracted with chloroform. The chloroform layer was washed with water and brine, dried over anhydrous sodium sulfate and concentrated in vacuo to an oil, which was chromatographed over 100 g. of silica gel by eluting with 3% methanol/97% chloroform mixtures. The product was collected and crystallized from ethyl acetate to yield 1-(dimethylamino)methyl-8-bromo-6-(2-pyridyl)-4H-s-triazolo[4,3-a][1,4]benzodiazepine of melting point 163.5°–165° C.

Anal. calcd. for $C_{18}H_{17}BrN_6$: C, 54.42; H, 4.31; N, 20.11; Br, 21.15; Found: C, 54,38; H, 4.29; N, 20.03; Br, 20.73.

EXAMPLE 4

8-Fluoro-1-[(dimethylamino)methyl]-6-(o-chlorophenyl)-4H-s-triazolo[4,3-a][1,4]benzodiazepine In the manner given in Example 1, 8-fluoro-6-(o-chlorophenyl)-4H-s-triazolo[4,3-a][1,4]benzodiazepine is treated with dimethylmethylene ammonium bromide to give 8-fluoro-1-[(dimethylamino)methyl]-6-(o-chlorophenyl)-4H-s-triazolo[4,3-a][1,4]benzodiazepine.

EXAMPLE 5

8-Fluoro-1-[(dimethylamino)methyl]-6-(2-pyridyl)-4H-s-triazolo[4,3-a][1,4]benzodiazepine In manner given in Example 5, 8-fluoro-6-(2-pyridyl)-4H-s-triazolo[4,3-a][1,4]benzodiazepine is treated with dimethylmethylene ammonium iodide to give 8-fluoro-6-(2-pyridyl)-s-triazolo[4,3-a][1,4]benzodiazepine.

EXAMPLE 6

8-Chloro-1-[(dimethylamino)methyl]-6-(o-chlorophenyl)-4-methyl-4H-s-triazolo[4,3-a][1,4]benzodiazepine In the manner given in Example 1, 8-chloro-6-(o-chlorophenyl)-4-methyl-4H-s-triazolo[4,3-a][1,4]benzodiazepine is treated with dimethylmethylene ammonium trifluoroacetate to give 8-chloro-1-[(dimethylamino)methyl-6-(o-chlorophenyl)-4-methyl]-4H-s-triazolo[4,3-a][1,4]benzodiazepine.

EXAMPLE 7

8-Chloro-1-[(dimethylamino)methyl]-6-(2-pyridyl)-4H-s-triazolo[4,3-a][1,4]benzodiazepine In the manner given in Example 5, 8-chloro-6-(2-pyridyl)-4H-s-triazolo[4,3-a][1,4]benzodiazepine is treated with dimethylmethylene ammonium hexachloroantimonic acid (HS6Cl₆) to give 8-chloro-6-(2-pyridyl)-4H-s-triazolo[4,3-a][1,4]benzodiazepine.

EXAMPLE 8

8-Fluoro-1-[(dimethylamino)methyl]-6-phenyl-4H-s-triazolo[4,3-a][1,4]benzodiazepine In the manner given in Example 1, 8-fluoro-6-phenyl-4H-s-triazolo[4,3-a][1,4]benzodiazepine is treated with dimethylmethylene ammonium chloride to give 8-fluoro-1-[(dimethylamino)methyl]-6-phenyl-4H-s-triazolo[4,3-a][1,4]benzodiazepine.

EXAMPLE 9

8-Trifluoromethyl-1-[(dimethylamino)methyl]-6-(2-pyridyl)-4H-s-triazolo[4,3-a][1,4]benzodiazepine In the manner given in Example 3, 8-trifluoromethyl-6-(2-pyridyl)-4H-s-triazolo[4,3-a][1,4]benzodiazepine is treated with dimethylmethylene ammonium iodide to give 8-trifluoromethyl-6-(2-pyridyl)-4H-s-triazolo[4,3-a][1,4]benzodiazepine.

EXAMPLE 10

8-Bromo-1-[(dimethylamino)methyl]-6-(o-chlorophenyl)-4H-s-triazolo[4,3-a][1,4]benzodiazepine In the manner given in Example 1, 8-bromo-6-(o-chlorophenyl)-4-H-s-triazolo[4,3-a][1,4]benzodiazepine is treated with dimethylmethylene ammonium iodide to give 8-bromo-1-[(dimethylamino)methyl]-6-(o-chlorophenyl)-4H-s-triazolo[4,3-a][1,4]benzodiazepine.

EXAMPLE 11

8-Nitro-1-[(dimethylamino)methyl]-6-(o-chlorophenyl)-4H-s-triazolo[4,3-a][1,4]benzodiazepine In the manner given in Example 1, 8-nitro-6-(o-chlorophenyl)-4H-s-triazolo[4,3-a][1,4]benzodiazepine is treated with dimethylmethylene ammonium bromide to give 8-nitro-1-[(dimethylamino)methyl]-6-(o-chlorophenyl)-4H-s-triazolo[4,3-a][1,4]benzodiazepine.

EXAMPLE 12

8-Chloro-1-[(dimethylamino)methyl]-6-(o-fluorophenyl)-4H-s-triazolo[4,3-a][1,4]benzodiazepine In the manner given in Example 1, 8-chloro-6-(o-fluorophenyl)-4H-s-triazolo[4,3-a][1,4]benzodiazepine is treated with dimethylmethylene ammonium chloride to give 8-chloro-1-[(dimethylamino)methyl]-6-(o-fluorophenyl)-4H-s-triazolo[4,3-a][1,4]benzodiazepine.

EXAMPLE 13

1-[(Dimethylamino)methyl]-6-phenyl-4H-s-triazolo[4,3-a][1,4]benzodiazepine

In the manner given in Example 1, 6-phenyl-4H-s-triazolo[4,3-a][1,4]benzodiazepine is treated with dimethylmethylene ammonium chloride to give 1-[(dimethylamino)methyl]-6-phenyl-4H-s-triazolo[4,3-a][1,4]benzodiazepine.

EXAMPLE 14

1-[(Dimethylamino)methyl]-6-(2-pyridyl)-4H-s-triazolo[4,3-a][1,4]benzodiazepine

In the manner give in Example 5, 6-(2-pyridyl)-4H-s-triazolo[4,3-a][1,4]benzodiazepine is treated with dimethylmethylene ammonium chloride to give 1-[(dimethylamino)methyl]-6-(2-pyridyl)-4H-s-triazolo[4,3-a][1,4]benzodiazepine.

EXAMPLE 15

8-Trifluoromethyl-1-[(dimethylamino)methyl]-6-(o-chlorophenyl)-4H-s-triazolo[4,3-a][1,4]benzodiazepine In the manner given in Example 1, 8-trifluoromethyl-6-(o-chlorophenyl)-4H-s-triazolo[4,3-a][1,4]benzodiazepine is treated with dimethylmethylene ammonium chloride to give 8-trifluoromethyl-1-[(dimethylamino)methyl]-6-(o-chlorophenyl)-4H-s-triazolo[4,3-a][1,4]benzodiazepine.

EXAMPLE 16

7-Chloro-1-[(dimethylamino)methyl]-6-phenyl-4H-s-triazolo[4,3-a][1,4]benzodiazepine In the manner given in Example 1, 7-chloro-6-phenyl-4H-s-triazolo[4,3-a][1,4]benzodiazepine is treated with dimethylmethylene ammonium chloride to give 7-chloro-1-[(dimethylamino)methyl]-6-phenyl-4H-s-triazolo[4,3-a][1,4]benzodiazepine.

EXAMPLE 17

7-Bromo-1-[(dimethylamino)methyl]-4-methyl-6-(2-pyridyl)-4H-s-triazolo[4,3-a][1,4]benzodiazepine In the manner given in Example 5, 7-bromo-3-methyl-6-(2-pyridyl)-4H-s-triazolo[4,3-a][1,4]benzodiazepine is treated with dimethylmethylene ammonium chloride to give 7-bromo-1-[(dimethylamino)methyl]-3-methyl-6-(2-pyridyl)-4H-s-triazolo[4,3-a][1,4]benzodiazepine.

By the process given in the preceeding examples other 1-[(dimethylamino)methyl]-6-(substituted)-4H-s-triazolo[4,3-a][1,4]benzodiazepines can be produced such as:
9-trifluoromethyl-1-[(dimethylamino)methyl]-6-phenyl-4H-s-triazolo[4,3-a][1,4]benzodiazepine;
10-fluoro-1-[(dimethylamino)methyl]-6-(o-chlorophenyl)-4H-imidazo[4,3-a][1,4]benzodiazepine;
10-bromo-1-[(dimethylamino)methyl]-6-(o-fluorophenyl)-4H-s-triazolo[4,3-a][1,4]benzodiazepine;
10-nitro-1-[(dimethylamino)methyl]-6-phenyl-4H-s-triazolo[4,3-a][1,4]benzodiazepine;
7-nitro-1-[(dimethylamino)methyl]-6-phenyl-4H-s-triazolo[4,3-a][1,4]benzodiazepine;
7-bromo-1-[(dimethylamino)methyl]-4-methyl-6-phenyl-4H-s-triazolo[4,3-a][1,4]benzodiazepine;
10-trifluoromethyl-1-[(dimethylamino)methyl]-4-methyl-6-phenyl-4H-s-triazolo[4,3-a][1,4]benzodiazepine;
9-bromo-1-[(dimethylamino)methyl]-4- methyl-6-phenyl-4H-s-triazolo[4,3-a][1,4]benzodiazepine;
9-nitro-1-[(dimethylamino)methyl]-2,4-dimethyl-6-(o-chlorophenyl)-4H-s-triazolo[4,3-a][1,4]benzodiazepine;
1-[(dimethylamino)methyl]-6-(o-chlorophenyl)-4H-s-triazolo[4,3-a][1,4]benzodiazepine;
10-trifluoromethyl-1-[(dimethylamino)methyl]-6-(2-pyridyl)-4H-s-triazolo[4,3-a][1,4]benzodiazepine;
9-bromo-1-[(dimethylamino)methyl]-6-(2l -pyridyl)-4H-s-triazolo[4,3-a]2l,4]benzodiazepine;
10-bromo-1-[(dimethylamino)methyl]-6-(2-pyridyl)-4H-s-triazolo[4,3-a][1,4]benzodiazepine;

9-nitro-1-[(dimethylamino)methyl]-6-(2-pyridyl)-4H-s-triazolo[4,3-a][1,4]benzodiazepine;

and the like.

I claim:

1. A process for the production of 1-[(dimethylamino)methyl]-6-substituted-4H-s-triazolo[4,3-a][1,4]benzodiazepines of the formula II:

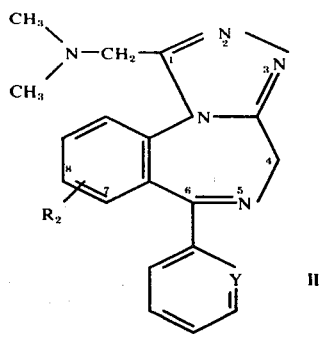

wherein Y is nitrogen or

in which $R_1$ is hydrogen, fluoro, or chloro; and wherein $R_2$ is hydrogen, fluoro, chloro, bromo, trifluoromethyl, or nitro; which comprises:

treating a compound of formula I:

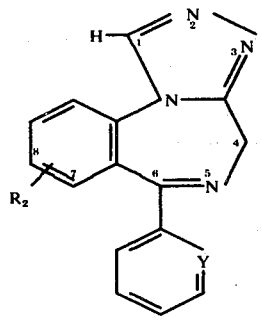

wherein $R_2$ and Y are defined as above, in solution, between 50°–100° C. with a compound of formula IV

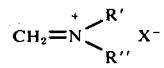

wherein $X^-$ is the anion of a monovalent inorganic or organic acid, to yield the corresponding compound of formula II above.

2. The process of claim 1, wherein the compound of formula IV

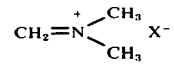

$X^-$ is the anion of hydrochloric, hydrobromic, hydriodic, or trifluoroacetic acid.

3. The process of claim 1, wherein the preferred starting product I has the substituent $R_3$ in the 8-position and $R_1$ is hydrogen.

4. The process of claim 2, wherein the preferred starting compound has the substituent $R_3$ in the 8-position and $R_1$ is hydrogen.

5. The process of claim 1, wherein the starting compound is selected from the group consisting of 8-chloro-6-(o-chlorophenyl)-4H-s-triazolo[4,3-a][1,4]benzodiazepine; and 8-bromo-6-(2-pyridyl)-4H-s-triazolo[4,3-a][1,4]benzodiazepine.

6. A process for the production of 8-chloro-1-[(dimethylamino)methyl]-6-phenyl-4H-s-triazolo[4,3-a][1,4]benzodiazepine which comprises: treating a compound of the formula:

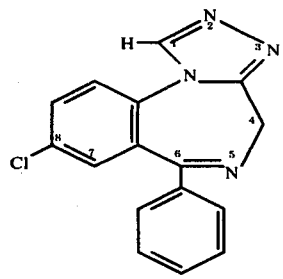

in dimethylformamide, at 50° to 100° C., with

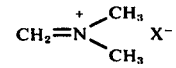

wherein $X^-$ is the anion of hydrochloric, hydrobromic, hydriodic or trifluoroacetic acid.

7. The process of claim 6, wherein the temperature of the reaction is between 50° to 60° C.

* * * * *